(12) United States Patent
Loeb (10) Patent No.: US 11,350,870 B2
(45) Date of Patent: Jun. 7, 2022

(54) METHOD OF IDENTIFYING EPILEPTIC BRAIN REGIONS

(71) Applicant: THE BOARD OF TRUSTEES OF THE UNIVERSITY OF ILLINOIS, Urbana, IL (US)

(72) Inventor: Jeffrey A Loeb, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 386 days.

(21) Appl. No.: 16/012,843

(22) Filed: Jun. 20, 2018

(65) Prior Publication Data

US 2018/0360372 A1    Dec. 20, 2018

Related U.S. Application Data

(60) Provisional application No. 62/522,122, filed on Jun. 20, 2017.

(51) Int. Cl.
| | | |
|---|---|---|
| *A61B 5/00* | (2006.01) | |
| *A61B 5/055* | (2006.01) | |
| *A61B 5/145* | (2006.01) | |
| *G01R 33/465* | (2006.01) | |
| *G01N 24/08* | (2006.01) | |

(52) U.S. Cl.
CPC .......... *A61B 5/4094* (2013.01); *A61B 5/055* (2013.01); *A61B 5/14546* (2013.01); *A61B 5/4064* (2013.01); *G01N 24/08* (2013.01); *G01R 33/465* (2013.01)

(58) Field of Classification Search
CPC ... A61B 5/055; A61B 5/14546; A61B 5/4064; A61B 5/4094; G01N 24/08; G01R 33/465
See application file for complete search history.

(56) References Cited

U.S. PATENT DOCUMENTS

| | | | | |
|---|---|---|---|---|
| 5,887,588 A | * | 3/1999 | Usenius ................. | A61B 5/055 600/410 |
| 2014/0221482 A1 | * | 8/2014 | Mochel ................. | A61B 6/037 514/547 |
| 2018/0052177 A1 | * | 2/2018 | Atzori ................ | G01N 33/6896 |

OTHER PUBLICATIONS

Kwan & Brodie, 2000, Early identification of refractory epilepsy. New Engl. J. Med. 342, 314-319.
Engel, 1993, Update on surgical treatment of the epilepsies. Neurology, vol. 43 1612-1617.
Mikuni et al., 2006, A step-by-step resection guided by electrocorticography for nonmalignant brain tumors associated with long-term intractable epilepsy. Epilepsy Behav. 8, 560-564.
Mittal et al., 2016, Intracranial EEG analysis in tumor-related epilepsy: Evidence of distant epileptic abnormalities. Clin. Neurophysiol. 127, 238-244.
Tao et al., 2005, Intracranial EEG substrates of scalp EEG interictal spikes. Epilepsia 46, 669-676.

(Continued)

*Primary Examiner* — Pascal M Bui Pho
*Assistant Examiner* — Alexei Bykhovski
(74) *Attorney, Agent, or Firm* — McDonnell Boehnen Hulbert & Berghoff LLP (57) ABSTRACT

This disclosure provides methods, reagents, and diagnostic and prognostic markers useful for non-invasive identification, diagnosis, and therapeutic intervention in individuals with epilepsy. More particularly, the disclosure uses specific metabolites measured by magnetic resonance spectroscopy in brain tissue to detect epileptic brain regions.

4 Claims, 7 Drawing Sheets

(56) References Cited

OTHER PUBLICATIONS

Peeling & Sutherland, 1993, 1H magnetic resonance spectroscopy of extracts of human epileptic neocortex and hippocampus. Neurology 43, 589-594.
Garcia, Laxer & Ng, 1995, Application of spectroscopic imaging in epilepsy. Magn. Reson. Imaging 13, 1181-1185.
Pan & Kuzniecky, 2015, Utility of magnetic resonance spectroscopic imaging for human epilepsy. Quant. Imaging Med. Surg. 5, 313-22.
Maudsley et al., 2010, Application of volumetric MR spectroscopic imaging for localization of neocortical epilepsy. Epilepsy Research, 88(2-3), 127-138.
Maudsley et al., 2009, Mapping of brain metabolite distributions by volumetric proton MR spectroscopic imaging (MRSI). Magnetic Resonance in Medicine, 61(3), 548-559.
Maudsley et al., 2009, Reproducibility of serial whole-brain MR Spectroscopic Imaging. NMR in Biomedicine, 23(3), 251-256.
Gotman, 1991, Relationships between interictal spiking and seizures: human and experimental evidence. The Canadian journal of neurological sciences. Le journal canadien des sciences neurologiques 18, 573-576.
Asano et al., 2003, Quantitative interictal subdural EEG analyses in children with neocortical epilepsy. Epilepsia 44, 425-434.
Bautista, Cobbs, Spencer, & Spencer, 1991, Prediction of surgical outcome by interictal epileptiform abnormalities Turing intracranial EEG monitoring in patients with extrahippocampal seizures. Epilepsia 40, 880-890).
White et al., 2010, EEG spike activity precedes epilepsy after kainate—induced status epilepticus. Epilepsia 51, 371-383.
Loeb, 2011, Identifying targets for preventing epilepsy using systems biology. Neurosci. Lett. 497, 205-212.
Loeb, 2010, A human systems biology approach to discover new drug targets in epilepsy. Epilepsia 51 Suppl 3, 171-177.
Dachet et al., 2015, Predicting novel histopathological microlesions in human epileptic brain through transcriptional clustering. Brain, 138:356-370.
Rakhade et al., 2005, A common pattern of persistent gene activation in human neocortical epileptic foci. Annals of Neurology 58,736-747.
Beaumont et al., 2012, Layer-Specific CREB Target Gene Induction in Human Neocortical Epilepsy. Journal of Neuroscience 32, 14389-14401.
Cheng et al., 1996, Enhanced resolution of proton NMR spectra of malignant lymph nodes using magic-angle spinning. Magn. Reson. Med. 36, 653-658.
Cheng et al., 1997, Quantitative neuropathology by high resolution magic angle spinning proton magnetic resonance spectroscopy. Proc. Natl. Acad. Sci. USA 94, 6408-6413.
Ghoddoussi et al., 2010, Methionine sulfoximine, an inhibitor of glutamine synthetase, lowers brain glutamine and glutamate in a mouse model of ALS. Journal of the Neurological Sciences 290, 41-47.
Klunk et al., 1994, Analysis of magnetic resonance spectra by mole percent: comparison to absolute units. Neurobiology of aging 15, 133-140.
Højsgaard et al., 2005, The R Package geepack for Generalized Estimating Equations. Journal of Statistical Software 15, 1-11.
Robin et al., 2011, pROC: an open-source package for R and S+ to analyze and compare ROC curves. BMC bioinformatics 12, 77.
Dziuban & Shirkey, 1974, When is a correlation matrix appropriate for factor analysis? Some decision rules. Psychological Bulletin 81, 358-361.
Liang & Zeger, 1986, Longitudinal data analysis using generalized linear models. Biometrika 73, 13-22.
Podo, 1999, Tumour phospholipid metabolism. NMR Biomed. 12, 413-439.
Farooqui et al., 1997, Phospholipase A2 and Its Role in Brain Tissue. J. Neurochem. 69, 889-901.
Visioli et al., 1993, Free fatty acid and diacylglycerol accumulation in the rat brain during recurrent seizures is related to cortical oxygenation. J. Neurochem. 61, 1835-1842.
Priel & Albuquerque, 2002, Short-Term Effects of Pilocarpine on Rat Hippocampal Neurons in Culture. Epilepsia 43, 40-46.
Cavalheiro et al., 1991, Long-term effects of pilocarpine in rats: structural damage of the brain triggers kindling and spontaneous recurrent seizures. Epilepsia 32, 778-782.
Benjamini & Hochberg, 1995, Controlling the false discovery rate: a practical and powerful approach to multiple testing. Journal of the Royal Statistical Society. Series B (Methodological), 289-300.
Kamburov et al., 2013, The ConsensusPathDB interaction database: 2013 update. Nucleic acids research 41, D793-800.
de Cannes et al., 1998, Metabolic and cellular characterization of immortalized human microglial cells under heat stress. Neurochem. Int. 33, 61-73.
Sada et al., 2015, Targeting LDH enzymes with a stiripentol analog to treat epilepsy. Science 347:1362-1367.

* cited by examiner

METHOD OF IDENTIFYING EPILEPTIC BRAIN REGIONS

CROSS REFERENCE

This application claims priority to U.S. Provisional Patent Application Ser. No. 62/522,122 filed Jun. 20, 2017, the disclosure of which is incorporated by reference herein in its entirety.

STATEMENT OF GOVERNMENTAL INTEREST

This invention was made with government support under grant nos. R56 NS083527, R01 NS045207 and R01 NS058802 awarded by the National Institutes of Health. The government has certain rights in this invention.

TECHNICAL FIELD

This disclosure provides methods, reagents, and diagnostic and prognostic biomarkers useful for non-invasive identification, diagnosis, and therapeutic intervention in individuals with seizure disorders including epilepsy. More particularly, the disclosure provides methods for detecting epileptic brain regions in brain tissue using specific metabolites measured by magnetic resonance spectroscopy. Additional embodiments provide a panel of metabolites for use in the methods provided herein.

BACKGROUND OF THE DISCLOSURE

Epilepsy is a disorder of recurrent seizures that affects 50 million people worldwide, and medication management is ineffective in up to 30% of these patients (Kwan & Brodie, 2000, Early identification of refractory epilepsy. *New Engl. J. Med.* 342, 314-319). In patients whose seizures start from focal brain regions, surgery that removes electrically active brain regions can be curative, however, these regions can be difficult to identify. Precise localization of these inciting regions is pivotal to treatment success, but frequently requires invasive implantation of recording electrodes directly on the brain surface or within the brain itself (Engel, 1993, *Neurology*, Vol. 43 1612-1617). While some patients develop epilepsy in response to a lesion (e.g., injury, tumor, or stroke), the regions of brain that produce seizures are often well outside the margins of the lesion and should be resected for optimal outcome (Mikuni et al., 2006, A step-by-step resection guided by electrocorticography for non-malignant brain tumors associated with long-term intractable epilepsy. *Epilepsy Behav.* 8, 560-564; Mittal et al., 2016, Intracranial EEG analysis in tumor-related epilepsy: Evidence of distant epileptic abnormalities. *Clin. Neurophysiol.* 127, 238-244).

Epilepsy has been a challenging disease to diagnose and develop novel treatments due to limitations in non-invasive methods to identify epileptic brain regions. Scalp EEG recordings can reliably detect epileptic discharges occupying at least 10 $cm^2$ of brain tissue (Tao et al., 2005, Intracranial EEG substrates of scalp EEG interictal spikes. *Epilepsia* 46, 669-676). However, EEG recording does not allow detection of most brain regions because the regions are too small. Additionally, EEG recording cannot be universally applied because the recordings require invasive methods for implantation of the electrodes into the brain.

There is thus a need in this art for reliable biomarkers to be identified and non-invasive methods for detecting them that would greatly help in localizing epileptic brain regions for surgery in addition to being informative for clinical trials and diagnosis.

SUMMARY OF THE DISCLOSURE

This disclosure provides reagents, methods and biomarkers for identifying and providing therapeutic intervention for individuals with epileptic brain regions.

In particular embodiments provided herein are methods of identifying epileptic regions of the brain comprising measuring the concentration of one or a plurality of metabolites in brain tissue using magnetic resonance spectroscopy wherein the metabolites are choline, glycerophosphorylcholine, γ-aminobutyric acid, glutamine, glutamate, myo-inositol, lactate, N-acetylaspartate, N-acetylaspartylglutamate, phosphorylcholine, phosphorylethanolamine, taurine and/or creatine plus phosphocreatine or any informative combination thereof and wherein one or a plurality of metabolites exhibit an epilepsy-associated concentration.

Also provided herein are methods of treating an epileptic subject by surgically removing an epileptic portion of the subject's brain identified by measuring concentrations of one or a plurality of metabolites using magnetic resonance spectroscopy wherein the metabolites are choline, glycerophosphorylcholine, γ-aminobutyric acid, glutamine, glutamate, myo-inositol, lactate, N-acetylaspartate, N-acetylaspartylglutamate, phosphorylcholine, phosphorylethanolamine, taurine and/or creatine plus phosphocreatine, or any informative combination thereof.

In particular embodiments, the metabolites are choline, creatine plus phosphocreatine, glycerophosphorylcholine, myo-inositol, lactate, N-acetylaspartylglutamate, phosphorylcholine, and/or phosphorylethanolamine, or any informative combination thereof. In particular embodiments, the concentration of choline is reduced, the concentration of creatine plus phosphocreatine is increased, the concentration of glycerophosphorylcholine is increased, the concentration of myo-inositol is reduced, the concentration of lactate is reduced, the concentration of N-acetylaspartylglutamate is increased, the concentration of phosphorylcholine is reduced, and/or the concentration of phosphorylethanolamine is reduced in the epileptic brain region.

In particular embodiments, the metabolites are choline, creatine plus phosphocreatine and/or lactate, or any informative combination thereof. In particular embodiments, the concentration of choline is reduced, the concentration of creatine plus phosphocreatine is increased, and/or the concentration of lactate is reduced.

In particular embodiments, the methods disclosed herein include comparing measured levels of the metabolites with a pre-determined control, wherein changes in the measured concentration of the metabolites relative to the pre-determined control is indicative of the epileptic region of the brain. In particular embodiments, the pre-determined control is derived from measured concentration of the metabolites in non-epileptic brain tissue. In particular embodiments, the non-epileptic brain tissue comprises non-epileptic tissue from the subject's brain.

In particular embodiments, the methods disclosed herein include using measured levels of metabolites simultaneously as predictor variables in a metabolite-based generalized estimating equation logistic regression model to discriminate between epileptic and non-epileptic regions of the brain.

In particular embodiments, the magnetic resonance spectroscopy is $^1$H MRS.

Specific preferred embodiments of the present disclosure will become evident from the following more detailed description of certain preferred embodiments and the claims.

BRIEF DESCRIPTION OF THE DRAWINGS

FIG. 1A is a schematic diagram illustrating experimental design of methods disclosed herein. Human brain tissues were removed as part of planned surgery for refractory epilepsy. Regions of high and low spiking were identified based on long-term subdural electrocorticography. Each section of tissue was precisely mapped to the overlying subdural electrode and then split into two halves. One half was used for histology while cortical gray matter was isolated from the other half. The cortical gray matter was then further divided into two portions, half of which was used to generate RNA for microarray analysis while the other half was used for high-resolution magic angle spinning $^1$H MRS (HR-MAS $^1$H MRS).

FIGS. 2A-2C illustrate that the logistic regression described herein demonstrates the existence of a consistent metabolomic signature. Logistic regression using 8 metabolites demonstrated high sensitivity and specificity in discriminating high spiking tissue samples from low (left) spiking tissue samples.

FIGS. 3A-3D illustrate correlational analysis between metabolites, gene expression and histology that suggest an alerted metabolic state in high spiking human brain.

FIGS. 4A-4B illustrates that logistic regression performed using the maximum 14 components obtained from principal components analysis demonstrated high sensitivity and specificity in discriminating high-spiking tissue samples from low-spiking tissue samples.

FIG. 5 is a schematic diagram illustrating a putative model of metabolomic and genomic involvement in generating seizure activity. Differences in metabolite levels between high and low spiking brain regions likely reflects a state of increased metabolic demand leading to a chronic hypoxia with compensatory angiogenesis and preferential use of lactate as an alternative fuel source. Persistent epileptiform activity can also lead to synaptic remodeling involving both anabolic and catabolic processes, which may work together to reinforce the epileptic state. The different tiles indicate changes observed using metabolomics, histologic, and genomic techniques, respectively.

DETAILED DESCRIPTION

All publications, patents and patent applications cited herein are hereby expressly incorporated by reference for all purposes.

Before describing the present invention in detail, a number of terms will be defined. As used herein, the singular forms "a," "an," and "the" include plural referents unless the context clearly dictates otherwise. For example, reference to "an active ingredient" means one or more active ingredients.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the term "about" refers to ±10% of any particular value.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z."

Provided herein are non-invasive methods for identifying and providing therapeutic intervention for individuals with epileptic brain regions. The metabolites identified herein provide a highly predictive pattern of expression corresponding to brain regions showing high levels of epileptic activity. The methods disclosed herein advantageously enable non-invasive differentiation of epileptic brain regions form normal brain regions using unique metabolomic-genomic differences for high-spiking epileptic human brain.

In particular embodiments, provided herein are methods of identifying epileptic regions of the brain in a subject comprising measuring the concentration of one or a plurality of metabolites in brain tissue from a subject using magnetic resonance spectroscopy wherein the metabolites are choline, glycerophosphorylcholine, γ-aminobutyric acid, glutamine, glutamate, myo-inositol, lactate, N-acetylaspartate, N-acetylaspartylglutamate, phosphorylcholine, phosphorylethanolamine, taurine and/or creatine plus phosphocreatine, or any informative combination thereof and wherein one or a plurality of metabolites exhibit an epilepsy-associated concentration.

As used herein, "Cho" means free choline, "Cr+PCr" means creatine plus phosphocreatine, "GABA" means γ-aminobutyric acid, "Gln" means glutamine, "Glu" means glutamate, "GPC" means glycerophosphorylcholine, "myo-Ins" means myo-inositol, "Lac" means lactate, "MM140" means macromolecules at 1.4 ppm, "NAA" means N-acetylaspartate, "NAAG" means N-acetylaspartylglutamic acid, "PCh" means phosphorylcholine, "PE" means phosphorylethanolamine and "Tau" means taurine.

In another embodiment, the metabolites are choline, creatine plus phosphocreatine, glycerophosphorylcholine, myo-inositol, lactate, and N-acetylaspartylglutamate, phosphorylcholine, and/or phosphorylethanolamine, or any informative combination thereof.

In another embodiment, the metabolites are choline, creatine plus phosphocreatine, glycerophosphorylcholine, myo-inositol, lactate, N-acetylaspartylglutamate, phosphorylcholine, and/or phosphorylethanolamine, or any informative combination thereof. In particular embodiments, a reduction in one or more measured levels of choline, myo-inositol, lactate, phosphorylcholine and phosphorylethanolamine relative to control and/or an increase in the measured levels of creatine plus phosphocreatine, glycerophosphorylcholine, and N-acetylaspartylglutamate relative to control is indicative of an epileptic region of the brain. In another embodiment, the metabolites are choline, creatine plus phosphocreatine and/or lactate, or any informative combination thereof. In particular embodiments, a reduction in measured levels of choline and lactate relative to control and/or an increase in the measured level of creatine plus phosphocreatine relative to control is indicative of an epileptic region of the brain.

As used herein the term "biomarker" refers to a compound or molecule, in a biosample that has a predictive value for one or more diseases. The presence, absence, reduction and/or upregulation of the biomarker may be associated with and/or be indicative of a particular disease such as epilepsy. Determination of the level or activity of a biomarker in the sample may comprise the detection and quantification of the biomarker itself or of a precursor, derivative or metabolite thereof.

As used herein "metabolite" refers to a substance that is involved in metabolism (e.g., product of or necessary for metabolism).

In one embodiment, magnetic resonance spectroscopy (MRS) is used to measure concentrations of the desired metabolites. MRS is a technique for characterizing compounds associated with tissue metabolism with high translational potential since it can be applied to both intact tissue samples ex vivo as well as animal models and human patients in vivo. While there are numerous MRS-visible atomic nuclei, $^1$H spectroscopy tends to be the most common by virtue of its high sensitivity and the numerous compounds it is capable of probing. Previous $^1$H MRS studies of epilepsy have demonstrated perturbations in the neurochemistry of epilepsy patients and have assisted in efforts to lateralize the epileptic focus (Peeling & Sutherland, 1993, 1H magnetic resonance spectroscopy of extracts of human epileptic neocortex and hippocampus. *Neurology* 43, 589-594; Garcia, Laxer & Ng, 1995, Application of spectroscopic imaging in epilepsy. *Magn. Reson. Imaging* 13, 1181-1185; Pan & Kuzniecky, 2015, Utility of magnetic resonance spectroscopic imaging for human epilepsy. *Quant. Imaging Med. Surg.* 5, 313-322).

MRS is a commonly used method for patients with a variety of brain disorders. MRS acquisition protocols and data processing methods are known in the art. See, for example, Maudsley et al., 2006, Comprehensive processing, display and analysis for in vivo MR spectroscopic imaging. *NMR in Biomedicine*, 19(4), 492-503. doi:10.1002/nbm.1025; Maudsley et al., 2009, Mapping of brain metabolite distributions by volumetric proton MR spectroscopic imaging (MRSI). *Magnetic Resonance in Medicine*, 61(3), 548-559. doi:10.1002/mrm.21875; Maudsley et al., 2010, Application of volumetric MR spectroscopic imaging for localization of neocortical epilepsy. *Epilepsy Research*, 88(2-3), 127-138. doi:10.1016/j.eplepsyres.2009.10.009; and Maudsley et al., 2009, Reproducibility of serial whole-brain MR Spectroscopic Imaging. *NMR in Biomedicine*, n/a-n/a. doi:10.1002/nbm.1445.

In particular embodiments, disclosed herein are methods for identifying epileptic regions of the brain in a subject non-invasively using a specific pattern of metabolite expression on MRS Spectroscopy. In an embodiment, the magnetic resonance spectroscopy is $^1$H MRS.

Epilepsy as used herein includes but is not limited to partial seizures such as temporal lobe epilepsy, absence seizures, generalized seizures, and tonic/clonic seizures.

As used herein, "epileptic brain region" means a region of the brain having a pattern of brain activity associated with an epileptic condition. The brain activity can occur before or during a seizure that is recognized as activity associated with an epileptic condition.

Epileptic regions of the brain produce abnormal synchronous discharges involving large populations of neurons. These discharges can remain isolated, as in the case of interictal discharges, or they can propagate and affect large regions of the brain, resulting in seizures. While the exact relationship between interictal spiking and seizures is not understood (Gotman, 1991, Relationships between interictal spiking and seizures: human and experimental evidence. *The Canadian journal of neurological sciences. Le journal canadien des sciences neurologiques* 18, 573-576), their localization is highly concordant (Asano et al., 2003, Quantitative interictal subdural EEG analyses in children with neocortical epilepsy. *Epilepsia* 44, 425-434) and the removal of both regions is associated with improved surgical outcome (Bautista, Cobbs, Spencer, & Spencer, 1991, Prediction of surgical outcome by interictal epileptiform abnormalities during intracranial EEG monitoring in patients with extrahippocampal seizures. *Epilepsia* 40, 880-890). Animal studies have shown that interictal activity may precede and hence be a biomarker of seizure development (White et al., 2010, EEG spike activity precedes epilepsy after kainate-induced status epilepticus. *Epilepsia* 51, 371-383).

The methods provided herein can be performed on a biosample isolated from a subject such as brain tissue, blood, and cerebral fluid. As used herein, "subject" refers to a warm-blooded animal such as a mammal, preferably a human, which is afflicted with, or has the potential to be afflicted with one or more diseases and disorders described herein.

A "control level" as used herein refers to an amount or range of amounts of metabolites found in a comparable biosample in subjects not suffering from epilepsy. The control level can also be based on a database of metabolites from previously tested subjects who did not have epilepsy. In an embodiment, the measured level of the metabolites is compared with a pre-determined control, wherein changes in the measured concentration of the metabolites relative to the pre-determined control is indicative of the epileptic region of the brain. In an embodiment, the pre-determined control is derived from the measured concentration of the metabolites in non-epileptic brain tissue. In an embodiment, the non-epileptic brain tissue comprises brain tissue from the same subject.

In particular embodiments, measured levels of the metabolites are used simultaneously as predictor variables in a metabolite based generalized estimating equation logistic regression model to discriminate between epileptic and non-epileptic regions of the brain. In particular embodiments, the logistic regression model is generated from human epileptic brain low and high spiking tissue samples using a generalized estimating equation logistic regression model with an exchangeable covariance matrix implemented. The model uses a repeated measures approach to help account for within-subject variability. Receiver Operating Characteristic (ROC) curves, a measure of model performance, calculated, together with a bootstrap estimated 95% confidence interval of the model sensitivity. The resultant factor scores are used as predictors in the logistic regression model, which uses a sample's measured metabolite profile to determine a predicted probability ($\hat{p}$) that the sample was a high spiking sample.

The logistic regression model described herein can identify epileptic brain regions relative to non-epileptic brain regions (pre-determined control regions) in all brain regions creating a probability map of epileptic and non-epileptic brain regions over the entire human brain. Three-dimensional data can be displayed to a clinician and can have the following uses:

1. Diagnosing whether or not someone has epilepsy, even prior to clinical seizures.
2. For use as a clinical/surrogate biomarker for epilepsy in clinical trials to test new drugs and devices to treat epilepsy.
3. Identifying epileptic brain regions to guide surgical planning of removing these to cure epilepsy.
4. For use in other human brain disorders and animal models of those disorders where epileptic discharges are present, including but not limited to, neuropsychiatric disorders such as attention deficit hyperactivity disorder and autism, neurodegenerative disorders, such as Alzheimer's, and many disorders known to produce seizures, including brain tumors, brain injuries, and strokes.

As used herein, the term "seizure disorder" refers to a condition characterized by the occurrence of a seizure. A seizure refers to an abnormal electrical discharge in the brain, and signs or symptoms resulting from such an abnormal discharge.

The methods of the invention can be used to treat seizure disorders including various forms of epilepsy. Epilepsy in its various forms is typically characterized by abnormal electrical discharges in the brain and often manifested by sudden brief episodes of altered or diminished consciousness, involuntary movements, or convulsions. Broadly speaking, forms of epilepsy can be divided into localization-related epilepsies, generalized epilepsies, or epilepsies of unknown localization.

The methods provided herein permit therapeutic intervention based on identification and spatial localization of epileptic brain regions, such as for the surgical removal of the epileptic brain regions to treat epilepsy, early diagnosis of epilepsy, and as a biomarker for epilepsy to be used for testing of drugs and medical devices designed to prevent, reduce, or cure epilepsy. In particular embodiments, the methods disclosed herein could be used following a head injury, stroke, or other brain disease where epilepsy could develop, to predict subjects likely to develop epilepsy to provide early interventions. In particular embodiments, the methods disclosed herein, can be used in clinical trials for testing of potential drugs or devices for treatment of epilepsy. This would dramatically reduce the time and cost of performing clinical trials by developing treatments that reduce the epileptic high spiking brain regions. In particular embodiments, the methods disclosed herein can be used in patients undergoing evaluation for epilepsy surgery as a means to localize precisely the epileptic brain tissues.

The terms "treatment" or "treat" as used herein refer to both therapeutic treatment and prophylactic or preventative measures. Those in need of treatment include those having a seizure disorder as well as those prone to have a seizure disorder or those in which a seizure disorder is to be prevented. In particular embodiments, the seizure disorder is epilepsy.

The invention will be further described in the following examples, which do not limit the scope of the disclosure described in the claims.

The Examples that follow are illustrative of specific embodiments of the disclosure and various uses thereof. They are set forth for explanatory purposes only and are not to be taken as limiting the disclosure.

EXAMPLES

Example 1: Materials and Methods

Human brain tissue samples from 9 human subjects with refractory epilepsy were obtained. All 9 subjects underwent a two-stage surgery, with long-term subdural electrocorticography (ECoG), consisting of initial electrode placement (Stage 1) for long-term recording and observation to optimize surgical resection (Stage 2) of seizure-generating areas. Table 1 illustrates profiles of patients with neocortical epilepsy and the corresponding tissue samples that were used. Spike frequency reflects epileptiform spike rates for both high- and low-spiking regions in the patient's brain, recorded in vivo using electrocorticography as their clinical treatment plan. Microarray characteristics show percent of genes that were at least 1.4 fold increased or decreased (after FDR correction to 1%) in expression in high-spiking relative to low-spiking samples. Documented tissue pathologies ("Other tissue diagnoses") were made from separate clinical tissue samples and were not present in the tissues used for the examples, which were normal appearing on histology. Abbreviations: AI=acute inflammation; BGW=blurring of grey-white junction; BSH=bifrontal subcortical heterotopias; CD=cortical dysplasia; CD?=probable cortical dysplasia; DG=diffuse gliosis; ES=epileptic spasms; H= heterotopia; MCD=mild cortical dysplasia; MG=mild gliosis; NA=data not available; NLP=normal laminar pattern; P=polymicrogyria; PC=partial complex; PE=periventricular mild increase in FLAIR; PO=porencephalic cyst; SG= secondary generalized (evolution from focal to bilateral, convulsive seizure); SupH=superficial heterotopia; TC= thickened cortex; W=increased white matter signal; WG=white matter gliosis.

spiking was classified as "low-spiking." In this manner, high- and low-spiking electrodes for each patient were identified and analyzed using both microarray and high-resolution magic angle spinning $^1$H MRS (HR-MAS $^1$H MRS) (HR-MAS 1H-MRS). Low-spiking electrodes were considered internal controls for each patient (Loeb, 2010, A human systems biology approach to discover new drug targets in epilepsy. *Epilepsia* 51 Suppl 3, 171-177). All tissue regions selected for use were free of apparent pathological changes and surgical hemorrhage based on gross examination and histology. Tissue histology studies were done as described in Dachet et al., 2015, Predicting novel histopathological microlesions in human epileptic brain through transcriptional clustering. *Brain*, 138:356-370.

Example 3: Agilent Microarrays

For microarray, total RNA was isolated from pooled alternating strips of full-thickness (layers I-VI) neocortical gray matter, helpful in averaging out small local differences.

TABLE 1

Patient clinical demographics and tissue information

| Patient | ILAE Classification | Age of Onset | Age of Surgery | Sex | Region | MRI Findings | Outcome (Engle 6 months) | Other tissue diagnoses | Spike Frequency | | Microarray Characteristics (% genes) | | |
|---|---|---|---|---|---|---|---|---|---|---|---|---|---|
| | | | | | | | | | Low | High | Increase | Decrease | Total |
| 1 | NA | NA | 10 | F | Temporal | PO | NA | DG, AI, NLP | 1 | 116 | 7.6 | 9.2 | 16.8 |
| 2 | SG | 9 | 11 | F | Frontal | BSH | NA | H | 0 | 5 | 2.6 | 5 | 7.5 |
| 3 | ES, PC | 0.4 | 3 | F | Parietal | PE | I | WG, SupH | 66 | 141 | 6.2 | 4.2 | 10.3 |
| 4 | ES | 0.5 | 3 | F | Temporal | BGW | I | MG | 56 | 212 | 4.9 | 5.4 | 10.2 |
| 5 | SG | NA | 7 | F | Frontal | P, W | I | CD, MG | 25 | 215 | 11.6 | 11.1 | 22.7 |
| 6 | ES | 2 | 6 | F | Frontal | TC, CD? | I | MG | 26 | 124 | 16.5 | 15 | 31.5 |
| 7 | ES | 0.5 | 8 | M | Parietal | NA | III | MG | 3 | 172 | 10.2 | 9.8 | 19.9 |
| 8 | PC, SG | 0 | 16 | M | Temporal | PO | I | DG | 44 | 176 | 6.9 | 10.6 | 17.5 |
| 9 | SG | 6 | 11 | F | Frontal | Normal | I | MCD | 2 | 66 | 4.8 | 4.1 | 8.9 |

Example 2: Subdural Electrocorticogrpahy

Figure 1A:
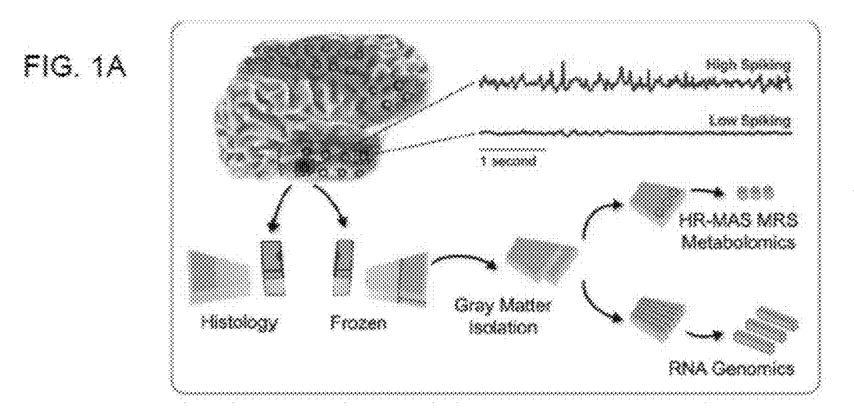
Figure 1B:
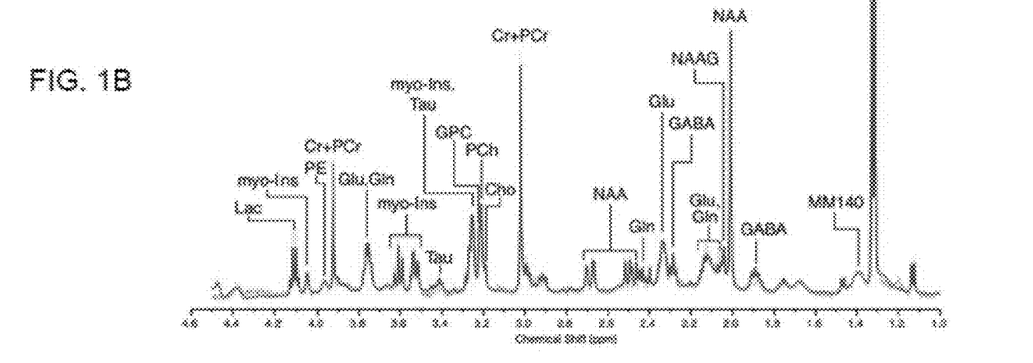
FIG. 1B is a representative high resolution spectrum of $^1$H HR-MAS MRS of human brain performed on partial thickness neocortical samples (Layers I-III). LC Model fitted spectrum (dark/thick line) shows excellent correspondence with averaged raw signal (light/gray line).

Electrically mapped regions of human neocortex from patients undergoing long-term invasive monitoring with electrocorticography (ECoG) using subdural grid electrodes were analyzed to localize regions that produce seizures and interictal spiking (Loeb, 2011, Identifying targets for preventing epilepsy using systems biology. *Neurosci. Lett.* 497, 205-212) (FIG. 1).

Interictal spiking activity was determined by averaging spike counts from 3 independent 10 min segments of ECoG recording, which were continuously recorded for at least 3 days prior to resection. Electrode placements were mapped precisely to their corresponding location on the neocortex using a combination of intraoperative electrode placement photos, as well as pre- and post-placement head CT, MRI, and X-rays. A sample block at each electrode location was removed and divided into two halves. One half was fixed in 4% paraformaldehyde for use in histological studies while the other half was stored frozen at −80° C. for further analysis (FIG. 1). Because of the great variance between patients in absolute spike frequency between regions considered for high- and low-spiking, the spike frequency was binarized into "high" and "low" spiking to reduce high-leverage effects. For each patient, the subdural electrode demonstrating the highest spiking frequency was classified as "high-spiking" and the electrode with the lowest or no A quadruplicate, flip-dye experimental design, as described (Rakhade et al., 2005, A common pattern of persistent gene activation in human neocortical epileptic foci. *Annals ofNeurology* 58, 736-747; Beaumont et al., 2012, Layer-Specific CREB Target Gene Induction in Human Neocortical Epilepsy. *Journal of Neuroscience* 32, 14389-14401), was used for each pair of high- and low-spiking samples within every patient. Briefly, labeled antisense RNAs were spin column purified and hybridized to human, genome-wide 60-mer oligonucleotide arrays (Catalog #G411A, Agilent), in a two-color dye-swap fashion. Differentially expressed genes were identified with a two-step hierarchical linear mixed model, correcting for array, dye, patient, array-die interactions and within-patient effects. Genes that had more than a 1.4-fold change between high and low spiking samples with a false discovery rate of <0.01 were considered to be differentially expressed. 990 such differentially expressed genes were identified from the 9 subject sample.

Example 4: High Resolution Magic Angle Spinning $^1$H MRS

Superior spectral resolution using an ultra-high field spectrometer at 500 MHz or 11.7 Teslas was used to determine whether epileptic human neocortex has a unique metabolomic signature. For each of the 9 patients discussed in Table 1, multiple regions with high versus low (or no) epileptic activity were compared using high-resolution magic angle spinning $^1$H MRS (HR-MAS $^1$H MRS), which allows for metabolite profiling of intact brain tissue (Cheng et al., 1996, Enhanced resolution of proton NMR spectra of malignant lymph nodes using magic-angle spinning. *Magn. Reson. Med.* 36, 653-658; Cheng et al., 1997, Quantitative neuropathology by high resolution magic angle spinning proton magnetic resonance spectroscopy. *Proc. Natl. Acad. Sci. USA* 94, 6408-6413).

For HR-MAS $^1$H-MRS, 3 mm punches were made of the apical neocortical gray matter (layers for each pair of high and low spiking samples within every patient in triplicate, at minimum, while frozen on solid $CO_2$. Tissue samples that were larger in size can have had more than 3 replicates. The median number replicates for low-spiking tissue was 4 with a range from 3 to 8 and the median number of replicates for high-spiking tissue was 6 with a range from 3 to 9. The frozen punches were analyzed using HR-MAS $^1$H-MRS on a 500 MHz (11.7 Tesla) Bruker Avance DRX-500 spectrometer as described by Ghoddoussi et al., 2010, Methionine sulfoximine, an inhibitor of glutamine synthetase, lowers brain glutamine and glutamate in a mouse model of ALS. *Journal of the Neurological Sciences* 290, 41-47). Mean singlet metabolite full width half max (FWHM) and SNR were 0.002±0.001 Hz and 34.3±8.41, respectively (mean±s.d). The samples were placed directly into a Bruker zirconium rotor containing 5 µL buffer (pH=7.4), $D_2O$, trimethylsilyl-proprionate (TSP) as the internal chemical shift reference (0.00 ppm), and formate for phase correction (8.44 ppm). The filled rotor was placed into a Bruker magic angle spinning probe maintained at 4° C. and spun at 4.2±0.002 kHz at 54.7° relative to the static magnetic field, $B_0$. Semi-automated and manual first- and second-order shimming was used to reduce field inhomogeneities. A rotor-synchronized 1-D Carr-Purcell-Meiboom-Gill (CP-MG) with $[90°-(\tau-180°-\tau)_n]$ pulse sequence was used to acquire tissue spectra (Cheng et al., 1996, Enhanced resolution of proton NMR spectra of malignant lymph nodes using magic-angle spinning. *Magnetic Resonance in Medicine* 36, 653-658). Twelve echo pulses were applied (n=12) with an inter-pulse delay ($\tau$) of 150 µs for TE=3.6 ms (echo time) and TR=6.21 s (repetition time). All spectra were acquired at a spectral bandwidth of 7 kHz (14 ppm) with 128 averages for a total acquisition time of approximately 13 min per sample.

The raw 1H MRS spectra were analyzed using LCModel with a custom, experimentally derived basis-set containing 27 individual neurochemical metabolite model spectra combined with modeled non-specific lipid and macromolecule signals. The concentration of the metabolites between 1.0 to 4.2 ppm were estimated and expressed in units of mmol per Kg wet weight. The precision and reliability of LCModel's fitted metabolite spectra to original data was estimated using Cramer-Rao Lower Bounds (CRLB). Only 14 metabolites whose average CRLB were less than or equal to 10% were used for further analysis. They were: choline, glycerophosphorylcholine (GPC), γ-aminobutyric acid (GABA), glutamine, glutamate, myo-inositol, lactate, N-acetylaspartate (NAA), N-acetylaspartylglutamate (NAAG), phosphorylcholine (PCh), phosphorylethanolamine (PE), taurine, simulated macromolecule at resonance position 1.40 ppm (MM140) and creatine plus phosphocreatine (Cr+PCr). Final metabolites concentrations are expressed as normalized mole percent of total metabolites, allowing measurements to be relatively insensitive to changes in extracellular volume (Klunk et al., 1994, Analysis of magnetic resonance spectra by mole percent: comparison to absolute units. *Neurobiology of aging* 15, 133-140).

Figure 4A:
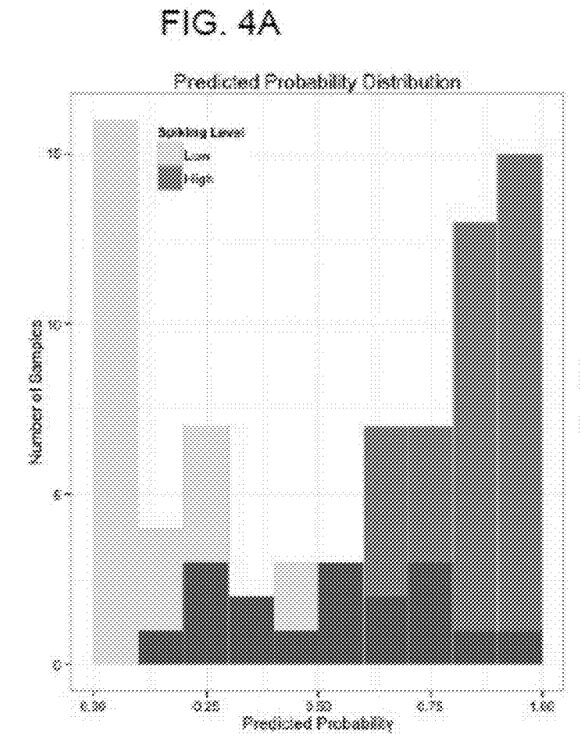
FIG. 4A shows the distribution of high- and low-spiking tissue samples (dark and light shading, respectively) and their predicted probabilities of being high spiking are illustrated in the histogram.
Figure 4B:
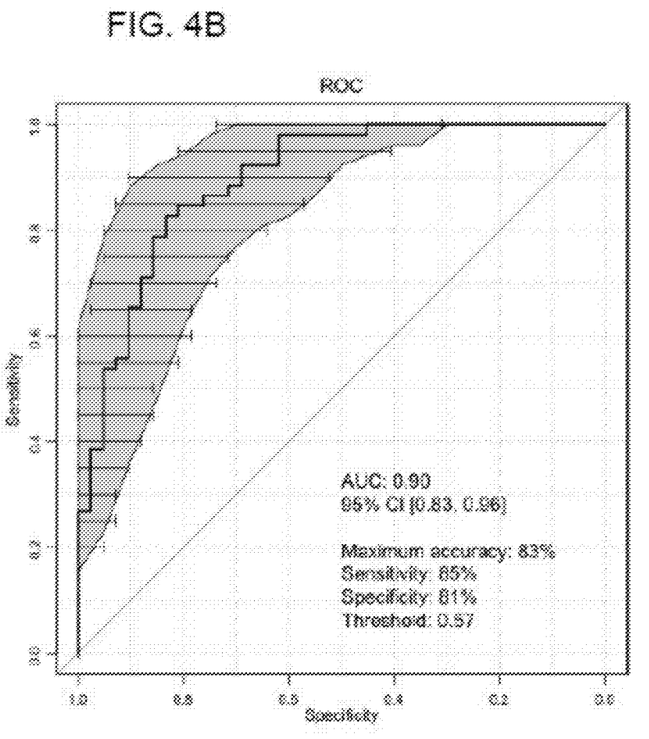
FIG. 4B shows the overall model performance characterized by a receiver operating characteristic (ROC) area under the curve (AUC) of 0.90, indicating excellent discrimination between high- and low-spiking tissues. Gray regions and horizontal error bars indicate the estimated 95% confidence intervals of sensitivity and specificity using non-parametric bootstrapping of 1000 samples.
Figure 5:
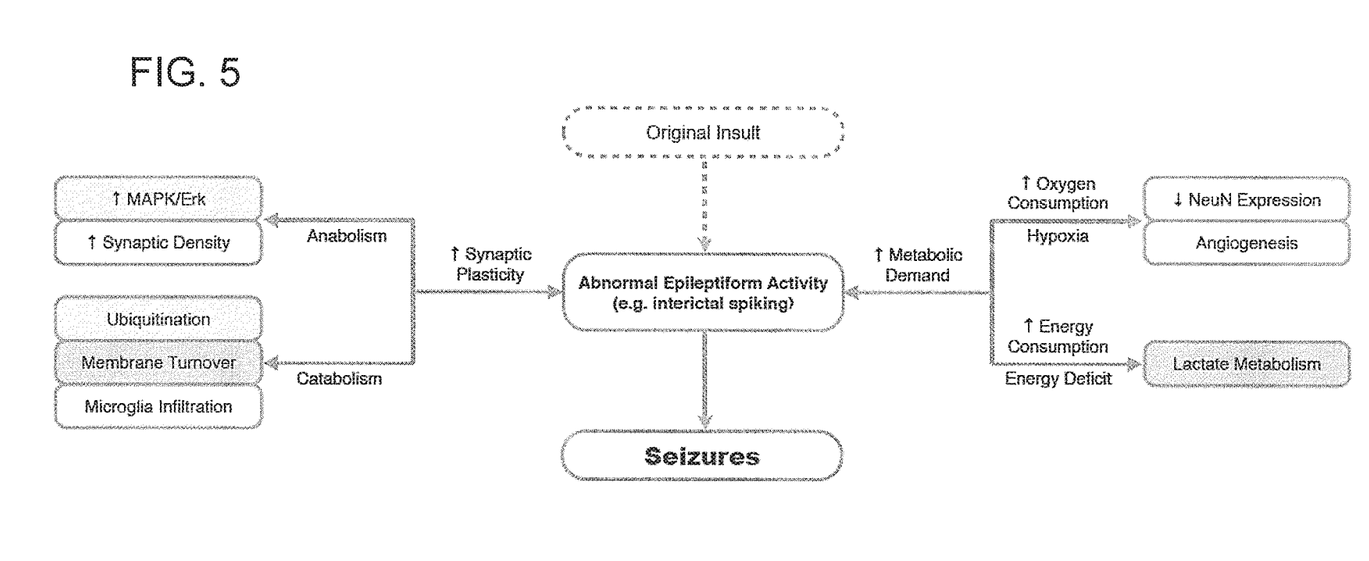

To determine whether or not there were detectable differences in metabolites between high- and low-spiking regions, a t-test was initially performed on all metabolites of interest to determine if significant differences exist between the metabolite in high- and low-spiking tissues. More refined classification and discrimination of high- and low-spiking samples using the metabolite profiles of all the samples were performed using generalized estimating equation (GEE) logistic regression model with an exchangeable covariance matrix implemented in R with geepack (Højsgaard et al., 2005, The R Package geepack for Generalized Estimating Equations. *Journal of Statistical Software* 15, 1-11; Team, 2014, R Foundation for Statistical Computing, Vienna, Austria) to help account for within-subject variability, since the samples were measured in multiplicates. Receiver Operating Characteristic (ROC) curves, as a measure of model performance, were calculated using pROC package, together with a bootstrap estimated 95% confidence interval of the model sensitivity (Robin et al., 2011, pROC: an open-source package for R and S+ to analyze and compare ROC curves. *BMC bioinformatics* 12, 77). Because several metabolites were highly correlated ($r > 0.8$) with each other, principal components analysis was initially used to address the issue of multicollinearity. Since the goal of the PCA analysis was to minimize multicollinearity, the maximum number of components possible (i.e., all 14 components) for the full model GEE logistic regression were included, in order to make predictions on whether a particular tissue sample is high- or low-spiking. The appropriateness of using the varimax orthogal rotation method of PCA was validated by both an adequate Kaiser-Meyer-Olkin measure of sampling accuracy (MSA=0.84) as well as significant Bartlett's test of sphericity, $\chi^2(91)=1109$, $p<0.001$, indicating that the data is appropriate for PCA analysis (Dziuban & Shirkey, 1964, When is a correlation matrix appropriate for factor analysis? Some decision rules. *Psychological Bulletin* 81, 358-361). The resultant factor scores were used as predictors in the logistic regression model, which used a given sample's measured metabolite profile to determine a predicted probability ($\hat{p}$) that the sample was a high spiking sample. The full 14 component model performed extremely well in discriminating high versus low spiking tissue with an ROC area under the curve (AUC) of 0.90, 95% CI (0.83, 0.96) (FIG. 4). For comparison, the AUC for the diagonal line on the ROC was 0.50, and represents the performance of chance classification (i.e., random guessing). A maximum accuracy of 83% along with 85% sensitivity and 81% specificity was achieved using cutoff threshold of 0.57, where all $\hat{p} \geq 0.57$ would be considered "high-spiking" while those below the cutoff would be considered "low-spiking." Gender was not included as a covariate in the model due to the highly uneven distribution between female (n=7) and male (n=2) participants. Effects of both region (based on electrode placement) and subject age were tested and determined to have insignificant effects on the model overall ($\chi^2$ (1)=0.213), and hence were removed from all analyses to reduce overfitting. The components playing a significant role (Wald p-values <0.10) in discriminating high- from low-spiking samples were identified and key metabolites were identified based on which metabolite had the highest loading factor on each component where the loading factor was at least 0.80.

Figure 2A:
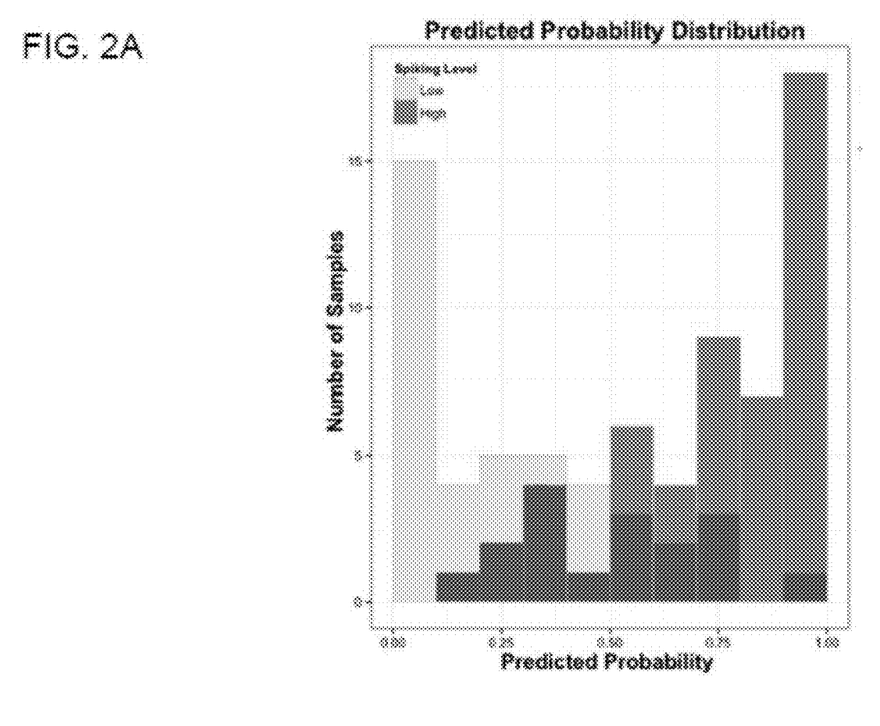
FIG. 2A is a histogram illustrating the distribution of high (dark gray) and low spiking tissue samples (light gray), respectively and their predicted probabilities of being high spiking.
Figure 2B:
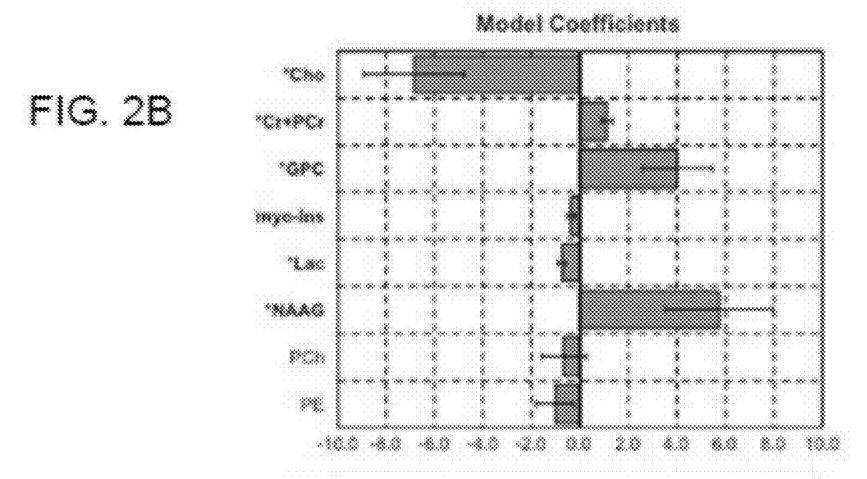
FIG. 2B illustrates model coefficients used for predicting high and low spiking tissue. Metabolites with significant ($p<0.05$) contributions to the model are bolded.
Figure 2C:
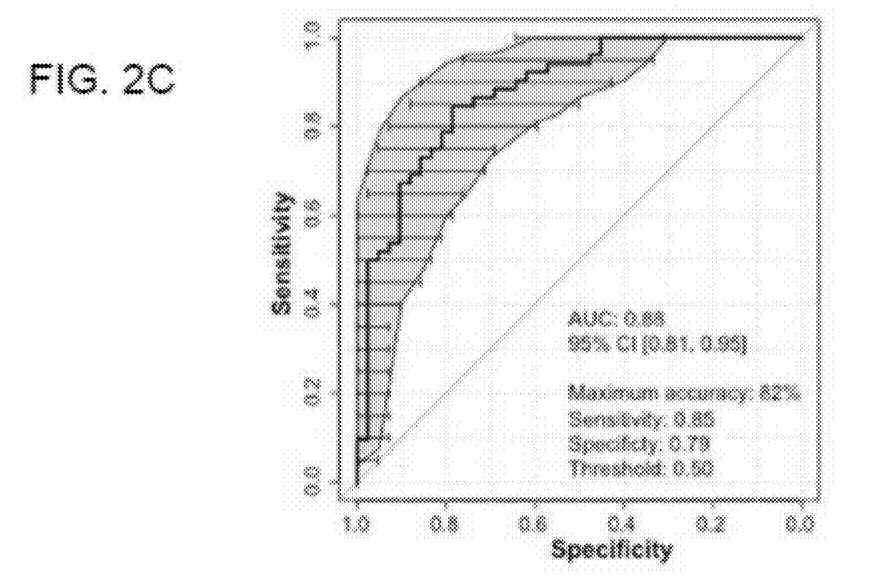
FIG. 2C is a graph showing overall model performance which is characterized by a receiver operating characteristic (ROC) area under the curve (AUC) of 0.88, indicating excellent discrimination between high and low spiking tissues. Gray regions and horizontal error bars indicate the estimated 95% confidence intervals of sensitivity and specificity using non-parametric bootstrapping of 1000 samples.

Mean values for the 14 metabolites in high-spiking and low-spiking tissue samples are summarized in Table 2. Statistically significant (p<0.05) differences between highand low-spiking tissues were found in 4 of 14 metabolites (in bold in Table 2) based on two-sample t-tests, namely choline, phosphorylcholine (PCh), lactate, and phosphorylethanolamine (PE). All were decreased in high-spiking tissue based on two-sample t-tests. All metabolites were normalized to the total fitted signals and expressed as percent total signal. Percent signal changes in high-spiking tissue samples relative to low-spiking tissue are also indicated for each metabolite in Table 2 (* $p<0.05$,  $p<0.01$, * $p<0.001$, uncorrected). Further analysis of all 14 metabolites using a combination principal components analysis and generalized estimating equation (GEE) (Liang & Zeger, 1986, Longitudinal data analysis using generalized linear models. *Biometrika* 73, 13-22) based logistic regression yielded a short list of 8 important metabolites: choline, Cr+PCr, lactate, myo-inositol, NAAG, PCh, GPC, and PE. Of these, 6 were identified to make significant contributions (Wald $p<0.05$) in differentiating high- versus low-spiking samples (FIG. 2 and Table 3). They were: choline, Cr+PCr, GPC, myo-inositol, lactate, and NAAG.

TABLE 2

Univariate analysis of metabolites

| Metabolite | Low Spiking Mean (SE) | High Spiking Mean (SE) | Percent Change | t-Test (p, 2-tailed) |
|---|---|---|---|---|
| * Cho | 0.61 (0.04) | 0.50 (0.02) | −19% | .01 |
| Cr + PCr | 8.55 (0.24) | 8.36 (0.21) | −2% | .56 |
| GABA | 3.13 (0.11) | 3.10 (0.09) | −1% | .79 |
| Gln | 3.75 (0.25) | 3.53 (0.15) | −6% | .44 |
| Glu | 7.03 (0.19) | 6.81 (0.21) | −3% | .44 |
| GPC | 0.58 (0.03) | 0.58 (0.03) | 0% | .98 |
| myo-Ins | 5.11 (0.22) | 4.63 (0.15) | −9% | .07 |
| * Lac | 15.06 (0.38) | 12.98 (0.48) | −14% | <0.001** |
| MM140 | 28.80 (1.62) | 32.17 (1.42) | 12% | .12 |
| NAA | 5.40 (0.20) | 5.21 (0.18) | −3% | .49 |
| NAAG | 0.99 (0.03) | 1.00 (0.03) | 1% | .78 |
| * PCh | 0.93 (0.04) | 0.78 (0.03) | −16% | <0.01** |
| * PE | 2.36 (0.09) | 2.11 (0.08) | −11% | .03 |
| Tau | 2.02 (0.09) | 2.03 (0.08) | 1% | .90 |

Table 3 illustrates logistic regression parameter estimates and odds ratios of metabolites included in the full predictive model. Significant metabolite predictors are indicated in bold and are in good agreement with results from the two-sample t-tests. Exponentiation of parameter estimates gives their corresponding odds ratios (OR). An OR greater than 1 indicates that for a given unit increase in the specified metabolite within a sample, there is also an increase in the probability of the tissue sample being high spiking. In contrast, an OR less than 1 indicates decrease in the likelihood that a tissue sample is high-spiking for a unit increase in the specified metabolite. Adjusted OR are odds ratios calculated for every 0.1 increment of a metabolite instead of the standard 1.0 increment used to calculated standard OR. It is important to note that the odds ratios are multiplied by for every unit increment in the predictor (i.e., metabolite levels) due to the exponential nature of logistic regression. For example, in the case of choline, a 0.20 unit increase in choline reduced the odds of the tissue being high spiking by a factor 0.26 (i.e., 0.51×0.51=0.26) (* $p<0.05$,  $p<0.01$, * $p<0.001$).

TABLE 3

Metabolite based logistic regression

| | Metabolite | Estimate (SE) | SE | 95% CI for Odds Ratio OR | Lower | Upper | Adjusted OR | Wald p-value |
|---|---|---|---|---|---|---|---|---|
| ** | (Intercept) | 0.41 (0.14) | 0.13 | 1.50 | 1.15 | 1.97 | 1.04 | <0.01 |
| *** | Cho | −6.83 (2.06) | 1.83 | 1.08E−03 | 1.92E−05 | 6.06E−02 | 0.51 | <0.001 |
| *** | Cr + PCr | 1.13 (0.22) | 0.34 | 3.09 | 2.02 | 4.72 | 1.12 | <0.001 |
| ** | GPC | 4.01 (1.45) | 1.39 | 55.3 | 3.20 | 9.56E+02 | 1.49 | <0.01 |
| * | myo-Ins | −0.37 (0.17) | 0.16 | 0.69 | 0.50 | 0.97 | 0.96 | .03 |
| *** | Lac | −0.74 (0.17) | 0.17 | 0.48 | 0.34 | 0.67 | 0.93 | <0.001 |
| ** | NAAG | 5.75 (2.22) | 0.09 | 315 | 4.08 | 2.43E+04 | 1.78 | <0.01 |
| | PCh | −0.67 (0.91) | 2.09 | 0.51 CV | 0.09 | 3.06 | 0.94 | .46 |
| | PE | −1.02 (0.76) | 0.81 | 0.36 | 0.08 | 1.59 | 0.90 | .18 |

The involvement of both choline and GPC suggests heightened cell membrane turnover in high spiking tissue. GPC and free fatty acids are key breakdown products of phosphatidylcholine, a major membrane constituent (Podo, 1999, Tumour phospholipid metabolism. *NMR Biomed.* 12, 413-439). This breakdown process can be initiated under hypoxic conditions with the calcium-dependent activation of phospholipase A2 ($PLA_2$), which is also responsible for release of arachidonic acid, a potent inflammatory intermediate (Farooqui et al., 2002, Phospholipase A2 and Its Role in Brain Tissue. *J. Neurochem.* 69, 889-901). Furthermore, in recurrent seizures, cortical oxygenation level has been shown to be inversely related to fatty acid release (Visioli et al., 1993, Free fatty acid and diacylglycerol accumulation in the rat brain during recurrent seizures is related to cortical oxygenation. *J. Neurochem.* 61, 1835-1842). Choline, also a key component in membrane turnover, is active both as a membrane precursor and as a membrane breakdown product from GPC degradation. Elevated acetylcholine receptor activation is known to increase seizure potential (Priel & Albuquerque, 2002, Short-Term Effects of Pilocarpine on Rat Hippocampal Neurons in Culture. *Epilepsia* 43, 40-46). Pilocarpine, an acetylcholine receptor agonist, is a relatively common agent used to generate seizures in animal models £Cavalheiro et al., 1991, Long-term effects of pilocarpine in rats: structural damage of the brain triggers kindling and spontaneous recurrent seizures. *Epilepsia* 32, 778-782; Pitkanen et al., 2005, Models of seizures and epilepsy. (Elsevier Academic, Oxford).

The logistic regression model performed well with Receiver Operating Characteristic (ROC) area under the curve (AUC) of 0.88, 95% CI [0.81, 0.95]. The optimal accuracy in classifying high- versus low-spiking using the metabolites was 82% with a sensitivity of 85% and specificity of 79%. In summary, this metabolomic signature presents a highly sensitive and specific new way to differentiate epileptic brain regions from their non-epileptic counterparts and provides a potential approach to non-invasively "visualize" epileptic brain regions clinically using $^1$H MRS.

Example 5: Integrative Analysis of Metabolomic, Transcriptional, and Histological Measures An integrative analysis of metabolomic, transcriptional, and histological measures were performed as outlined in FIG. 1. The metabolites of interest were used for additional correlational clustering studies to observe how changes in key metabolites corresponded to changes in gene expression and cell type distribution. Pearson correlations between the 990 differentially expressed genes (described above) across the 18 high- and low-spiking samples obtained from the 9 subjects and their corresponding mean metabolite concentrations for each sample were calculated (Dachet et al., 2015 Predicting novel histopathological microlesions in human epileptic brain through transcriptional clustering. *Brain,* 138:356-370). Linkages between two genes were created when Pearson correlations were ≥0.70. This cutoff was also consistent with an FDR of <0.07 (Benjamini & Hochberg, 1995, Controlling the false discovery rate: a practical and powerful approach to multiple testing. *Journal of the Royal Statistical Society. Series B (Methodological*), 289-300). Clusters were further analyzed using a combination of ConsensusPathDB (Kamburov et al., 2013, The ConsensusPathDB interaction database: 2013 update. *Nucleic acids research* 41, D793-800) and primary literature searches for functional and pathway enrichment. A cutoff threshold of FDR adjusted $p<0.05$ was used to identify potentially significant pathways associated with each metabolite-gene clusters. Additional associations between metabolites and putative cell types were explored using Pearson correlation based hierarchical clustering using the average linkage method. Cluster relationships were further characterized using the actual Pearson correlations themselves, where Pearson correlations ≥0.70 (FDR adjusted $p<0.05$) were considered statistically significant.

Two major clusters of gene-metabolite interactions emerged, centering on changes in energy state, with a down-regulation of lactate and upregulation of Cr+PCr (FIG. 3). Downregulated lactate clustered with a group of genes associated with G-protein coupled receptor signaling and angiogenesis pathways (FDR adjusted $p<0.01$), specifically VEGFA, FLT1, RGS1, RGS2, RHOU, GNA13, and TFRC, all of which were up-regulated in high-spiking brain regions. Also notable from the cluster was upregulation of multiple genes associated with ubiquitination, highly suggestive of the preferential involvement of the ubiquitin-proteasome pathway (UPP) in high spiking areas.

Figure 3A:
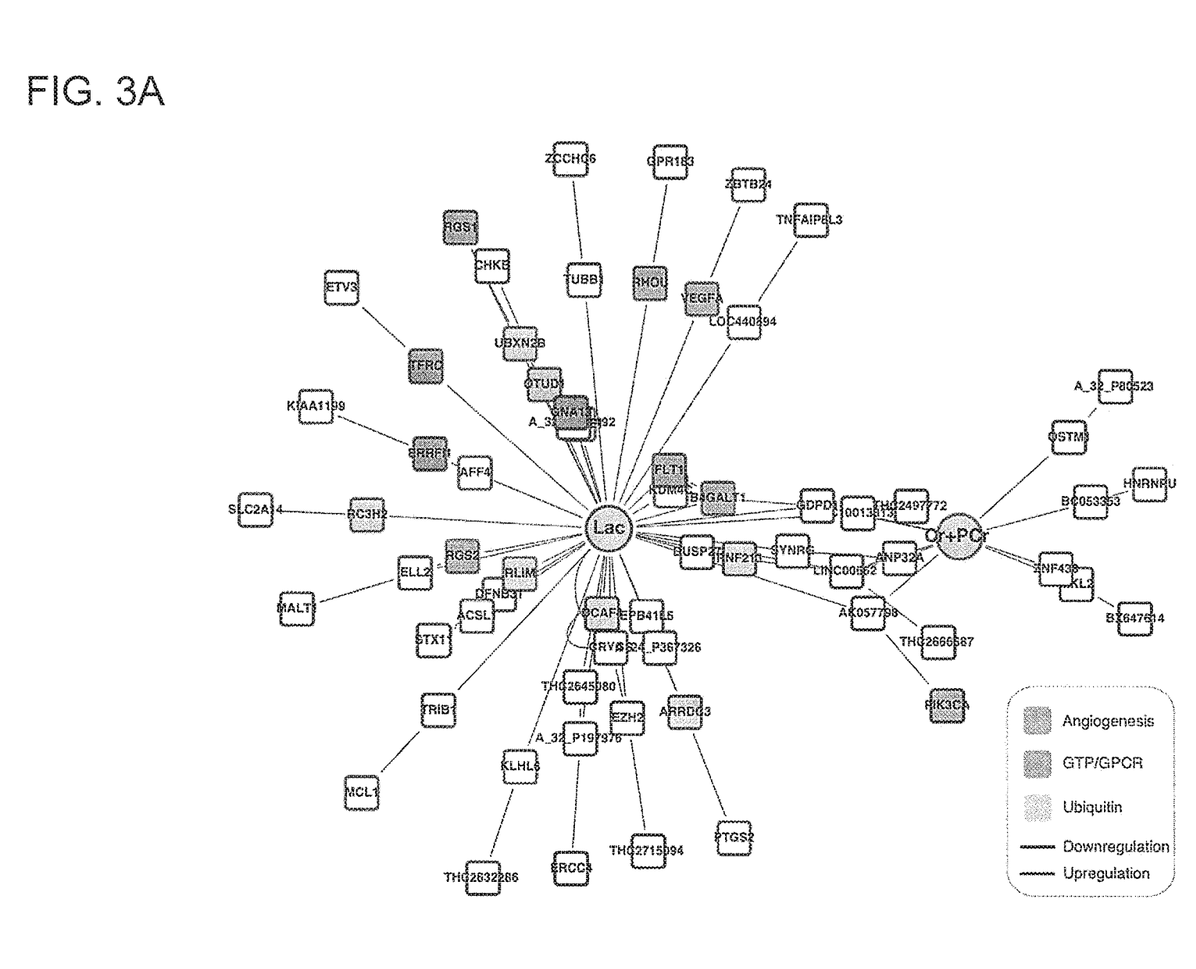
FIG. 3A illustrates correlational clustering between predictor metabolites and differentially expressed genes in high spiking tissue that demonstrates a large cluster of up-regulated genes around lactate, a negative predictor of high spiking. Upregulated genes are indicated in light gray and down-regulated genes are indicated in dark gray borders. Pathway enrichment analyses indicate many of these differentially expressed genes to be involved in G-protein signaling, angiogenesis, and also ubiquitination. Relevant genes in the lactate cluster include: Vascular endothelial growth factor A (VEGFA), Fms Related Tyrosine Kinase 1 (FLT1), Regulator Of G Protein Signaling 1 (RGS1), Regulator Of G Protein Signaling 2 (RGS2), Ras Homolog Family Member U (RHOU), G Protein Subunit Alpha 13 (GNA13), phosphatidylinositol 3-kinase (PK3CA), and Transferrin receptor protein 1(TFRC).
Figure 3B:
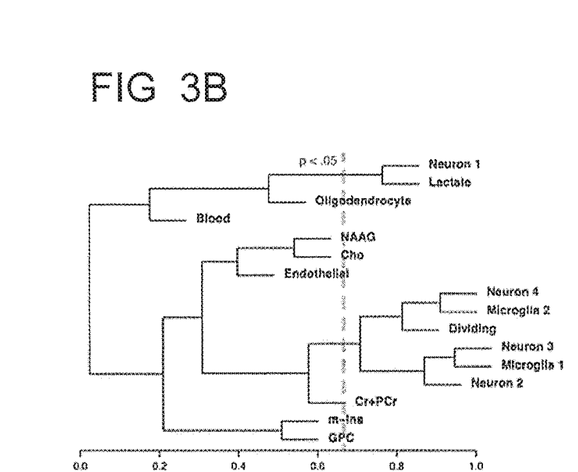
FIG. 3B illustrates that hierarchical clustering between metabolites and cell types showed significant associations between lactate and Neuron Type 1 (Neuron 1) and also between creatine plus phosphocreatine (Cr+PCr) and Microglia Type 1 (Microglia 1). The dashed vertical line indicates significance threshold of correlation, where paired relationships to the right of the line are significant.
Figure 3C:
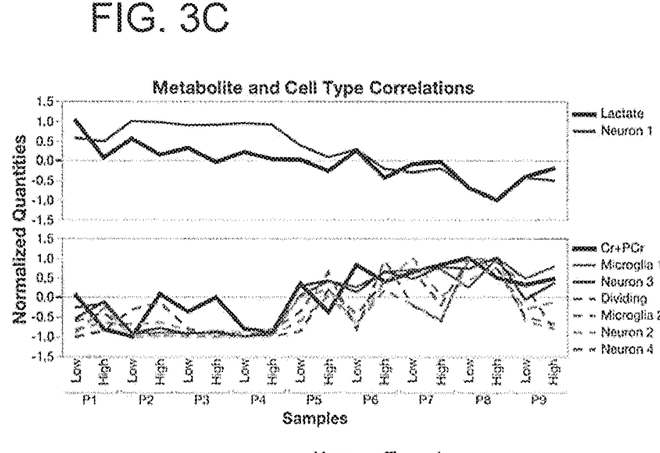
FIG. 3C illustrates normalized expression over all 18 samples between Lactate and Neuron Type 1 and between Cr+PCr and the cluster consisting of Microglia Type 1 and several other cell correlational clusters that showed stronger clustering between lactate, Cr+PCr and several cell types with the correlations between Microglia Type 1 and Neuron Type 3 being significant (solid lines). Other correlations in the same cluster, while not statistically significant, are also shown (dashed lines).
Figure 3D:
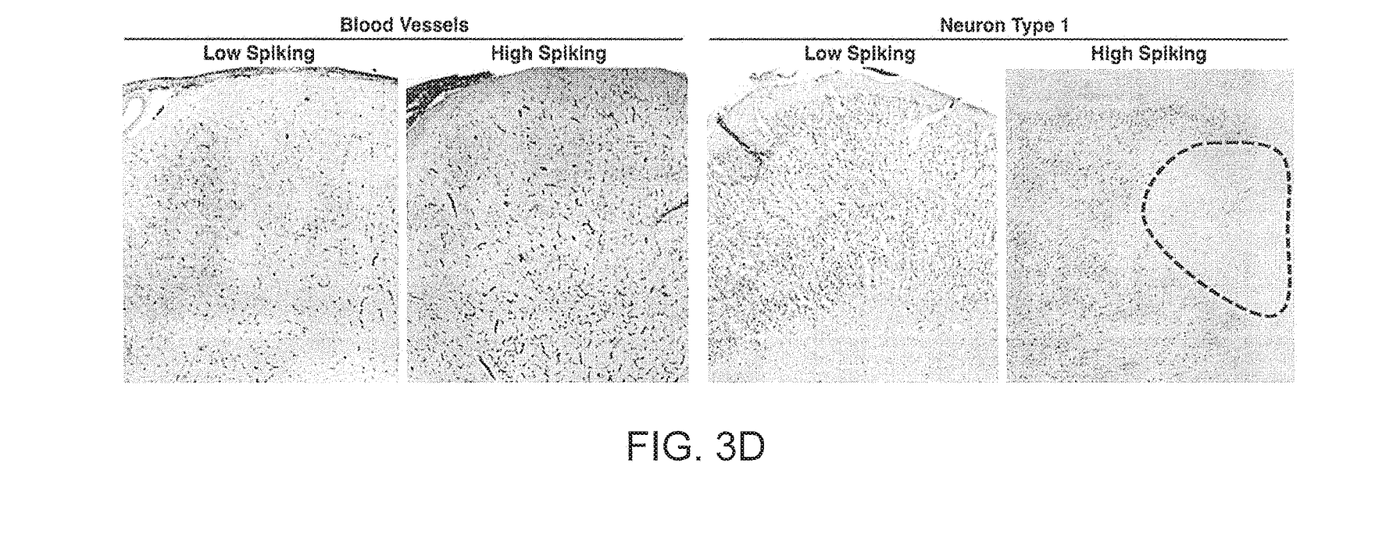
FIG. 3D shows representative histology from Patient 1 demonstrating increased blood vessels and the presence of microlesions (outlined) showing reduced NeuN staining in high-spiking tissue compared to its low-spiking counterpart.

Previously, a clustering approach to predict cell-type specific changes in regions of high versus low epileptic piking was developed and termed a "cellular interactome" was described in Dachet et al., 2015, Predicting novel histopathological microlesions in human epileptic brain through transcriptional clustering. *Brain* 138, 356-370. In Dachet et al., consistent differences were shown in high-spiking tissues that included increases in blood vessel density, inflammatory microglia, and millimeter-sized microlesions in deeper cortical layers. Id. These microlesions contained a unique population of neurons with reduced NeuN staining (Type 1 Neurons) and increased microglia (Type1 Microglia). Combining the cellular interactome of Dachet et al. with the present metabolomic dataset, significant correlations between reduced lactate and Neuron 1 ($r=0.76$; $p<0.05$) and increased Cr+PCr and Microglia 1 ($r=0.72$; $p<0.05$) (FIG. 3) were found. Both cell populations correlated with the degree of epileptic activity and the number of microlesions. Id. Histological examination of the specific tissue samples used here consistently showed an increase of microlesions and vascular density in high-versus low-spiking regions (FIG. 3). Specifically, reduced NeuN staining within microlesions that were found to be present in high numbers in human cortical epileptic brain regions was found. Id. Similarly, upregulation of Cr+PCr correlated with an increase of other neurons and Type 1 Microglia. Interestingly, microglia have also been shown to express high levels of PCr (de Gannes et al., 1998, Metabolic and cellular characterization of immortalized human microglial cells under heat stress. *Neurochem. Int.* 33, 61-73), which can explain Cr+PCr as a positive predictor of high-spiking activity.

Exactly why lactate is consistently downregulated in these brain regions was not clear. This can be due to unmet energy demands due to frequent interictal spiking leading to lactate consumption as an alternative energy source. Surgically excised tissue can be expected to become hypoxic and increase lactate levels, although the methods described here using multiple paired samplings of both high- and low-spiking samples from within the same patient should have controlled for this. Inhibition of lactate dehydrogenase, the key enzyme that coverts lactate to pyruvate for use in the TCA cycle, can cause hyperpolarization in neurons and suppress epileptiform activity (Sada et al., 2015, Targeting LDH enzymes with a stiripentol analog to treat epilepsy. *Science* 347:1362-1367). The strong relationship between lactate and the cluster of genes enriched in angiogenesis, revealed by correlational clustering, has been further validated by histological evidence of blood vessel proliferation in high spiking samples that may be compensatory to higher energy demands (Dachet et al., 2015, Predicting novel histopathological microlesions in human epileptic brain through transcriptional clustering. *Brain* 138, 356-370). A key feature of the epileptic brain regions is the presence of microlesions that show dramatic, focal reductions in synaptic connectivity. Id.

Taken together the combined genomic-metabolomic and cellular interactome data indicated the existence of a unique metabolomic-genomic signature linked to altered tissue energy demand and consumption in high-spiking brain tissue that could serve as a clinically translatable, non-invasive biomarker for the functional and structural abnormalities that underlie human neocortical epilepsy.

It is understood that the foregoing detailed description and accompanying examples are merely illustrative and are not to be taken as limitations upon the scope of the disclosure, which is defined solely by the appended claims and their equivalents.

The invention claimed is:

1. A method of treating an epileptic subject by surgically or otherwise removing or inactivating an epileptic portion of the subject's brain identified by
   (a) measuring concentrations of at least three metabolites in brain tissue from the subject's brain using magnetic resonance spectroscopy wherein the metabolites are choline, glycerophosphorylcholine, myo-inositol, lactate, N-acetylaspartylglutamate, phosphorylcholine, phosphorylethanolamine, and/or creatine plus phosphocreatine; wherein measuring concentrations of the at least three metabolites in the brain tissue includes measuring concentrations of at least three metabolites in the brain tissue as a pre-determined control;

(b) comparing measured concentrations of the at least three metabolites in the brain tissue from the subject's brain with the pre-determined control, wherein the measured concentrations of the at least three metabolites compared to the pre-determined control is indicative of the epileptic regions of the subject's brain; wherein the pre-determined control is derived from measured concentrations of the at least three metabolites in non-epileptic brain tissue, wherein the non-epileptic brain tissue comprises non-epileptic tissue from subjects without epilepsy and a known non-epileptic portion of the subject's brain tissue; and wherein the measured concentrations of the at least three metabolites in the brain tissue from the subject's brain comprise a reduced concentration of choline, an increased concentration of creatine plus phosphocreatine, an increased concentration of glycerophosphorylcholine, a reduced concentration of myo-inositol, a reduced concentration of lactate, an increased concentration of N-acetylaspartylglutamate, a reduced concentration of phosphorylcholine, or a reduced concentration of phosphorylethanolamine in the epileptic brain region compared to the pre-determined control; and (c) treating an epileptic subject by surgically or otherwise removing or inactivating an epileptic portion of the subject's brain identified as epileptic brain tissue in the subject's brain based on the compared measured concentrations of the at least three metabolites in the brain tissue from the subject's brain with the pre-determined control.

2. The method of claim 1 further comprising using measured levels of metabolites simultaneously as predictor variables in a metabolite-based generalized estimating equation logistic regression model to discriminate between epileptic and non-epileptic regions of the brain.

3. The method of claim 1 wherein the metabolites are choline, creatine plus phosphocreatine and lactate.

4. The method of claim 1 wherein the magnetic resonance spectroscopy is $^1$H MRS.

* * * * *